United States Patent
Jerala et al.

(10) Patent No.: US 12,304,966 B2
(45) Date of Patent: May 20, 2025

(54) SPLIT SUPERANTIGENS AND THEIR USE FOR IMMUNOTHERAPY

(71) Applicant: Kemijski Institut, Ljubljana (SI)

(72) Inventors: Roman Jerala, Ljubljana (SI); Anja Golob Urbanc, Kranj (SI)

(73) Assignee: KEMIJSKI INSTITUT, Ljubljana (SI)

( * ) Notice: Subject to any disclaimer, the term of this patent is extended or adjusted under 35 U.S.C. 154(b) by 467 days.

(21) Appl. No.: 16/629,009

(22) PCT Filed: Jun. 14, 2018

(86) PCT No.: PCT/SI2018/050019
§ 371 (c)(1),
(2) Date: Jan. 6, 2020

(87) PCT Pub. No.: WO2019/009819
PCT Pub. Date: Jan. 10, 2019

(65) Prior Publication Data
US 2020/0317805 A1    Oct. 8, 2020

(30) Foreign Application Priority Data
Jul. 5, 2017 (SI) ................... P-201700202

(51) Int. Cl.
| | |
|---|---|
| A61K 39/00 | (2006.01) |
| A61P 35/00 | (2006.01) |
| C07K 14/31 | (2006.01) |
| C07K 16/30 | (2006.01) |
| A61K 38/00 | (2006.01) |

(52) U.S. Cl.
CPC .............. C07K 16/30 (2013.01); A61P 35/00 (2018.01); C07K 14/31 (2013.01); *A61K 38/00* (2013.01); *A61K 2039/505* (2013.01); *C07K 2319/33* (2013.01); *C07K 2319/43* (2013.01); *C07K 2319/73* (2013.01)

(58) Field of Classification Search
CPC .......................... A61K 38/00; A61K 2039/505
See application file for complete search history.

(56) References Cited

PUBLICATIONS

Proft et al. (Clin. Exp. Immunol. Sep. 2003; 133 (3): 299-306).*
Hudson et al. (J. Exp. Med. Sep. 1, 1995; 182 (3): 711-20).*
Deacy et al. (Front. Immunol. 2021; 12: 731845; pp. 1-16).*
Zhang et al. (Toxins (Basel). Oct. 2013; 5 (10): 1859-71).*
Golob-Urbanc et al. (J. Biol. Chem. Apr. 19, 20199; 294 (16): 6294-305).*
Kozono et al. (Immunity. Aug. 1995; 3 (2): 187-96).*
Nur-ur Rahman et al. (J. Immunol. Dec. 15, 2006; 177 (12): 8595-603).*
Buelow et al. (J. Immunol. Jan. 1, 1992; 148 (1): 1-6).*
Golob-Urbanc et al. (J. Biol. Chem. Apr. 19, 2019; 294 (16): 6294-305).*
Dolberg et al. (Nat. Chem. Biol. May 2021; 17 (5): 531-9).*
Fujikawa et al. (Plant J. Oct. 2007; 52 (1): 185-95).*
Venetz et al. (J. Biol. Chem. Aug. 2, 20166; 291 (35): 18139-47).*
Stains et al. (ACS Chem. Biol. Oct. 15, 2010; 5 (10): 943-52).*
Mootz et al. (J. Am. Chem. Soc. Sep. 3, 2003; 125 (35): 10561-9).*
Sonntag et al. (Mol. Biosyst. Jun. 2011; 7 (6): 2031-9).*
Ozawa et al. (Anal. Chem. Dec. 15, 2001; 73 (24): 5866-74).*
Spanjaard et al. (Mol. Endocrinol. Jan. 1993; 7 (1): 12-6).*
Ghosh et al. (J. Am. Chem. Soc. 2000; 122 (23): 5658-9).*
Shekhawat et al. (Curr. Opin. Chem. Biol. Dec. 2011; 15 (6): 789-97).*
Gradiar et al. (J. Pept. Sci. Feb. 2011; 17 (2): 100-6).*
Pearce et al. (Adv. Biol. (Weinh). May 2021; 5 (5): e2000234; pp. 1-16).*
Antonoglou et al. (Front. Immunol. Jun. 30, 2020; 11: 1279; pp. 1-14).*
Kelcey G. Patterson et al, "Control of Established Colon Cancer Xenografts Using a Novel Humanized Single Chain Antibody-Streptococcal Superantigen Fusion Protein Targeting the 5T4 Oncofetal Antigen", www.plosone.org, PLOS One, vol. 9, No. 4, Apr. 15, 2014 (Apr. 15, 2014), e95200, pp. 1-10.
G. Forsberg et al, "Therapy of Human Non-Small-Cell Lung Carcinoma Using Antibody Targeting of a Modified Superantigen", www.bjcancer.com, British Journal of Cancer, Nature Publishing Group, GB, vol. 85, No. 1, Jul. 6, 2001 (Jul. 6, 2001), pp. 129-136.
Cecilia Gidlof et al, "A Superantigen-Antibody Fusion Protein For T-cell Immunotherapy of Human B-Lineage Malignancies.", www.bloodjournal.hematologylibrary.org, Blood, vol. 89, No. 6, Mar. 16, 1997 (Mar. 16, 1997), pp. 2089-2097.
Yongsheng Yu et al, "Functional Assembly of Protein Fragments Induced by Spatial Confinement", www.plosone.org, PLOS One, vol. 10, No. 4, Apr. 15, 2015 (Apr. 15, 2015), e0122101, pp. 1-13.
Amy E. Campbell et al, "Targeting protein function: the expanding toolkit for conditional disruption", Biochemical Journal, vol. 473, No. 17, Aug. 29, 2016 (Aug. 29, 2016), p. 2573-2589.

(Continued)

*Primary Examiner* — Stephen L Rawlings
(74) *Attorney, Agent, or Firm* — The Watson IP Group, PLC; Jovan N. Jovanovic (57) ABSTRACT

The invention refers to a split superantigen, divided into two fragments that by itself do not exhibit biologic activity, only upon dimerization they regain T cell activity. Scope of the invention is a screening method for detection of effective split superantigen designs, where split superantigen fragments are fused with coiled-coil forming peptides. The present invention relates to the field of cancer immunology. Each split superantigen fragment is fused with antibody or other tumor antigen specific protein, therefore only upon the binding of split superantigen-antibody fusion proteins to the tumor antigen, split superatigen fragments comes to proximity and reconstitute into biologically active form that activates T-cell response.

7 Claims, 5 Drawing Sheets

Specification includes a Sequence Listing.

(56) References Cited

PUBLICATIONS

Rishi Rakhit et al, "Chemical Biology Strategies for Post-translational Control of Protein Function", Chemistry and Biology, vol. 21, No. 9, Sep. 18, 2014 (Sep. 18, 2014), p. 1238-1252.
Lily Zhang et al, "Assessment of the Functional Regions of the Superantigen Staphylococcal Enterotoxin B", www.mdpi.com/journal/toxins, Toxins, vol. 5, No. 10, Oct. 22, 2013 (Oct. 22, 2013), p. 1859-1871.

* cited by examiner

SPLIT SUPERANTIGENS AND THEIR USE FOR IMMUNOTHERAPY

FIELD OF INVENTION

The field of invention is directed at a split superantigen, divided into two fragments that by itself do not exhibit any activity, only upon dimerization they regain T cell activity.

Scope of the invention is a screening method for detection of effective split superantigen designs, where split superantigen fragments are fused with coiledantigen, for purposes of cancer immunotherapy. Split superantigen design that proved efficacy when fused with coiled-coil forming peptides, was fused with antibody specific for tumor antigen. Hence only when antibody bound to the tumor antigen, split superantigen fragments came to proximity, dimerized and folded into biologically active form that activated T cell response, which lead to tumor cell death.

BRIEF DESCRIPTION OF THE DRAWINGS

FIG. 1A-C. Scheme of split superantigen fused with polypeptides. All gene constructs contain FLAG tag on the N-terminal end. Split superantigen fragments, N-terminal fragment (N-SEA) or C-terminal fragment (C-SEA), are fused with polypeptides P3 or P4 trough glycine-serine (GS) peptide linker. More specifically:

Row A: FLAG-N-SEA-GS-PE

Row B: FLAG-P4-GS-C-SEA

Row C: FLAG-P3-GS-C-SEA

FIG. 2. PBMC stimulation with split superantigen fused to polypeptides. 24 hours after seeding, PBMC were stimulated with 100 ng/ml commercially available superantigen (SEA) or with supernatant collected from HEK293T cells containing 50 μl of recombinant wildtype SEA (rSEA), 50 μl of split superantigen fused with polypeptides P3 or P4 (NP3, CP3, CP4), respectively, or with 25 μl of each split superantigen fragments fused with polypeptides P3 or P4, combined. After 24 hour incubation at 37° C., supernatant was collected and the production of human IL-2 was measured by ELISA assay.

FIG. 3A-B. Scheme of split superantigen fused with antibodies. All gene constructs contain His tag, composed of ten histidine amino residues, on the C-terminal end. Single chain variable fragment against tumor antigen CD20 (scFv-CD20) is fused with split superantigen fragments, N-terminal fragment (N-SEA) or C-terminal fragment (C-SEA), trough glycine-serine (GS) peptide linker. More Specifically:

Row A: scFV-CD20-GS-N-SEA

Row B: scFV-CD20-GS-C-SEA-His

FIG. 4. Binding assay. Raji cells were incubated with antibodies against HLA-DR,DP,DQ labeled with APC and/or antibodies against CD20 labeled with VioBlue. After 10 minutes of incubation in dark at 4° C., cells were washed. Cells were then incubated with 150 nM fusion proteins scFv-CD20/N-SEA (FIG. 4A) or scFv-CD20/C-SEA (FIG. 4B) for 1 hour at 37° C. After washed with PBS, cells were incubated 10 minutes in the dark at 4° C., with antibodies against His tag labeled with FITC. Binding of His-tagged fusion proteinsscFv-CD20/N-SEA and scFv-CD20/C-SEA to target antigen CD20 expressed on lymphoma cell line Raji was detected with flow cytometry.

FIG. 5. Cytotoxicity assay. Raji cells stained with CFSE were incubated with commercially available SEA (Sigma-Aldrich) and with different concentrations of fusion proteins scFv-CD20/N-SEA and/or scFv-CD20/C-SEA. After 1 h at 37° C. effector cells (PBMC) were added at ratios 1:10 or 1:20. Viability of tumor cells Raji was determined after 48 h at 37° C. Raji cells were stained with viability dyes, Annexin V-Pacific Blue (stain apoptotic cells) and TO-PRO-3 (stain necrotic cells), and analyzed on flow cytometry.

DETAILED DESCRIPTION

Unless defined otherwise, all technical and scientific terms used herein possess the same meaning as it is commonly known to experts in the field of invention. The terminology to be used in the description of the invention has the purpose of description of a particular segment of the invention and has no intention of limiting the invention. All publications mentioned in the description of the invention are listed as references. In the description of the invention and in the claims, the description is in the singular form, but also includes the plural form, what is not specifically highlighted for ease of understanding.

The present invention describes a new type of split proteins. The basis of the invention is the surprising discovery that toxins called superantigens can be divided into two fragments, each by itself not biologically active, they only acquire activity when dimerizing upon binding to cells that express tumor antigen on the surface.

One particular embodiment of the invention is a screening method for the detection of effective split superantigen designs. Split superantigen design is a challenging task, since it is impossible to predict the desirable split sites that would ensure that each split fragment by itself would not exhibit any activity, that the fragments would not reassemble spontaneously, and ideally, that reassembled split protein would have the activity comparable to wildtype protein. In most cases split proteins completely lose their biological activity or their activity is decreased in comparison to unsplit parent protein[18]. For detection of effective split protein designs it is desirable to have an easily measurable read out, as in case of for example split green fluorescent protein[19], where the read out is fluorescence. Depending on the fluorescence intensity it can be determined whether the biological activity of reassembled split protein is comparable to the activity of the unsplited parent protein, meanwhile in case of split superantigens, the read out is more complex. We establish a method for detection of effective split superantigen reassembly, based on split protein fusion with polypeptides. Split superantigen fragments fused with coiled-coil forming polypeptides are reassembled into a biologically active form meanwhile split superantigen fragments fused with polypeptides that do not form coiled-coil do not reassemble. Efficacy of split superantigen is determined based on biologic activity of reassembled protein. In order to monitor the biologic activity of split superantigen, human peripheral blood mononuclear cells (PBMC) were stimulated with fusion proteins (FIG. 1) and the release of human cytokine IL-2 was detected with ELISA assay. On the basis of IL-2 release we determined whether T cells were activated. The effective split superantigen variant was the one that activated T cells only when split superantigen was fused with coiled-coil forming polypeptides and did not activate T cell response when split superantigen was fused with polypeptides that do not form coiled-coil (FIG. 2).

Further, invention is based on the discovery, that split superantigen can be fused with target seeking moiety, such as antibody, specific for tumor antigen, which represents a new tool for treatment in the field of cancer immunotherapy. The binding of two antibodies specific for tumor antigens fused with split superantigen fragments, brings the inactive split fragments into close proximity so they can reassemble into biologically active form, cytotoxic to tumor cells expressing target antigen. The main advantage of the approach is the specificity only for tumor cells without affecting healthy cells expressing MHC class II, which, unlike the standard approach with wildtype superantigen, completely eliminates the toxic systemic effect of superantigen. At the same time, the invention further allows each split superantigen fragment to be coupled to an antibody specific for different tumor antigen, thereby increasing the selectivity of tumor cell recognition.

Definitions

The terms »homologue« and »orthologue« refer to polypeptides, originating from the same or different organism. The term »homologous« also refers to mutated protein segments, where the mutations have a minimal effect on the structure or function of the polypeptide. The term »mutant« refers to a polypeptide, differing from the native protein polypeptide in at least one amino acid.

The term »superantigen« refers to toxins from family of staphylococcal enterotoxins or streptococcal pyrogenic exotoxins secreted by the gram positive bacteria *Staphylococcus aureus* or *Streptococcus pyogenes*, their homologues, orthologues and mutants with preserved or enhanced basic function of superantigens.

The term »split superantigen« refers to complementary superantigen fragments, each by itself biologically inactive. Superantigen is split into two parts, an N-terminal fragment and a C-terminal fragment, that do not reassemble into an active form spontaneously. Split sperantigen fragments reassemble into biologically active form only when fused with coiled-coil forming peptides or when fused with antibody bind to tumor antigens. Split site can be located at any site in the superantigen, preferably in unstructured areas. At the same time, the number of overlapping amino acids between the N-terminal fragment and the C-terminal fragment of superantigen fragment is arbitrary.

The term »biologically active form« as used herein, refers to activity a superantigen may exhibit and means it is capable of binding to both MHC complex II and to the TCR which leads to activation of immune response.

The term »fragment« of molecule such as protein or nucleic acid refers to part of amino acid sequence or nucleic acid sequence.

The term »polypeptide« as used herein, refers to polypeptides that form specific dimers called coiled-coils only with its partner. The two polypeptides constituting the orthogonal pair can form parallel homodimers, antiparallel homodimers, or parallel heterodimers. Orthogonality in this case means that only one combination of two polypeptides forms a coiled-coil.

The term »coiled-coil« refers to secondary structure formed by pairs of polypeptides when dimerized. For the coiled-coil formation, it is essential that the polypeptide contains a distinct amino acid sequence. One turn in coiled-coil consists of 3,5 amino acid residues, therefore 2 turns represent about 1 nm long heptade. In the primary peptide structure, specific amino acid residues known to those skilled in the art are present at precisely determined sites in heptade repeat (sites a-b-c-d-c-f-g).

The term »antibody« refers to an immunoglobulin molecule, which is able to specifically bind to a target antigen. In the description of the invention, the term »antibody« is intendent to refer broadly to any immunologic binding agent such as polyclonal antibodies, monoclonal antibodies or antigen binding parts of the antibodies (for example $Fab(ab)_2$, Fab, Fv, scFv) known to those skilled in the art. The term »antibody«refers to any target seeking moieties, which are specific for tumor antigens, but are not limited to them. In addition to tumor specific antibodies, it is possible to use antibodies against different antigenic determinants, such as, for example, antigens involved in the development of autoimmune, viral diseases.

Superantigen fragments are linked together with polypeptides or antibodies by »peptide linker«, which is any polypeptide of any length and any amino acid sequence. The term »peptide linker« refers to amino acid sequences with the function of separating individual domains of a chimeric protein and to enable their proper spatial orientation.

The term »tag peptide« refers to amino acid sequences, added to a protein for simplified purification, isolation or detection.

The position of signal sequences, linker peptides and tag peptides can be arbitrary, although they should allow functional expression of the protein, while also preserving the function for which these sequences were selected, what is known to those skilled in the art.

The term »constitutive promoter« refers to a nucleotide sequence in DNA that provides a continuous transcription of structural genes and its location and sequence is known to those skilled in the art. The term »constitutive promoter« refers to a non-regulated promoter that allows a continuous expression of its associated gene. Suitable nucleotide sequences of constitutive promoters are known to those skilled in the art and described in the prior art.

The terms »promoter«, »teminator«, »protein«, »DNA« are generally known to persons skilled in the art and are used as expected.

The term »expression vector« refers to circular or linear DNA plasmids or viral DNA, containing operons listed in the invention and the necessary elements for expression in prokaryotic or eukaryotic cells, which are known to persons skilled in the art. Bacterial vectors contain bacterial control elements, a bacterial replication origin and an antibiotic resistance operon for selection of successfully transformed bacteria. Eukaryotic vectors contain, in addition to a bacterial replication origin, appropriate eukaryotic control elements, and appropriate antibiotic resistance operons for selection of successful bacterial transformation and/or successful eukaryotic transfection.

Embodiments of the invention can be used in prokaryotic as well as in eukaryotic organisms and cell lines using recombinant DNA technology. The basic difference is the use of appropriate nucleotide sequences in the promoter and the terminator known to those skilled in the art to ensure the structural gene transcription. One method of preparing fusion proteins is also chemical conjugation, wherein various heterobifunctional or heterobifunctional cross-linkers known to those skilled in the art are used to link the superantigen fragment with polypeptides or antibodies.

Transfer of DNA into host cells is performed with conventional methods well known to persons skilled in the arts, such as transformation, transduction or transfection, including: chemical transfer, electroporation, microinjection, DNA lipofection, cell sonication, gene bombarding, viral DNA transfer etc.

DNA transfer can be either transient or stable. »Transient transfer« refers to transfer of DNA in a vector that does not undergo cromosomal insertion. »Stable transfer« refers to insertion of DNA into the host genome. DNA transfer to a cell line with a previous stable insertion can be controlled with the presence of markers. »Markers« refer to antibiotic or chemical resistance and can be included in the vector or present on a separate vector.

Therefore one aspect of the present invention refers to split superantigen, wherein the superantigen is divided into two non-functional fragments that only in close proximity and when fused with coiled-coil forming peptides or fused with antibodies specific to tumor antigens, dimerize and form abiologically active superantigen. Split superantigen fragments are linked with the same or different proteins or polypeptides that, when bound to the target cell, induce the dimerization of inactive split superantigen fragments into the active superantigen. Proteins or polypeptides that trigger the dimerization of inactive split superantigen fragments into the active superantigen are identical or different and recognize the cell proteins expressed on the surface of the target cell, preferably antibodies or fragments of antibodies that recognize the surface proteins of the cells. These proteins or polypeptides preferably recognize the surface proteins on tumor cells.

Furthermore, the invention also relates to a screening method for detection of functional split superatnigens, wherein (a) combination of split superantigen fused with proteins that enable dimerization is provided and is preferably controlled and mediated chemically or by the presence of cells (b) split superantigen or cells expressing split superantigens is added to the reporter cells selected from any of the cells that are sensitive to the presence of active superantigen, preferably PBMC, and (c) measurement of superantigen activation by usage of reporter cells.

The present invention will now be further described. Examples of implementations described in detail below are conceived to best describe the invention. These descriptions are not intended to limit the field of the invention or its applicability, but serve to better demonstrate the invention and its applicability.

EXAMPLES

Example 1. Preparation of DNA Constructs for the Fusion Proteins According to the Invention For the preparation of DNA constructs the inventors used methods of molecular biology, such as: chemical transformation of competent *E. coli* cells, DNA plasmid isolation, polymerase chain reaction (PCR), PCR ligation, determination of nucleic acid concentration, agarose gel electrophoresis of DNA, isolation of DNA fragments from agarose gels, chemical synthesis of DNA, DNA digestion with restriction enzymes, digestion of plasmid vectors, ligation of DNA fragments, purification of plasmid DNA in larger quantities. Molecular cloning procedures are well known to the experts in the field and are described in details in molecular biology handbook[20].

All work was performed with sterile techniques, which are well known to persons skilled in the art. All plasmids, completed constructs and partial constructs were transformed into bacteria *E. coli* with chemical transformation. Plasmids and DNA constructs were transfected into HEK293T cell lines using commercially available transfection reagent polyethylenimine.

All DNA constructs have been prepared using techniques and methods known in the art. DNA constructs were inserted into appropriate plasmids suitable for eukaryotic or prokaryotic expression systems. Vectors used were commercially available, carrying all necessary features such as antibiotic resistance, origin of replication and multiple cloning site known to the experts in the field. The inventors confirmed adequacy of nucleotide sequences by sequencing and restriction analysis.

Example 2. Detection of Functional Split Superantigen by a Screening Method Based on Split Proteins Fused with Polypeptides a) Design of Split Superantigen Fused with Polypeptides In order to illustrate the invention well characterized staphylococcal enterotoxin A (SEA), from *Staphylococcus aureus*, was used as superantigen. Superantigen SEA was split into two fragments, an N-terminal fragment (1-120amino acid residues of SEA; SEQ ID: 1) and a C-terminal fragment (112-233 amino acid residues of SEA; SEQ ID NO: 2); which overlap in nine amino acid residues.

Both split SEA fragments were fused with polypeptides via the glycine-serine peptide linker (SEQ ID: 3). The orthogonal pair of polypeptides P3 (SEQ ID: 4) and P4 (SEQ ID: 5) [21] were selected as the most suitable dimerizing polypeptides to form coiled-coil.

Split superatnigens in fusion with polypeptides were prepared using recombinant DNA technology. Mammalian expression system, a human cell line HEK293T, was used. The methods and techniques of culturing cell cultures are well known to persons skilled in the art, therefore they are only briefly described in order to illustrate the embodiment. Cell line HEK293T was cultured at 37° C. and 5% $C0_2$. DMEM medium supplemented with 10% FBS, which contains all the necessary nutrients and growth factors, was used for cell culturing. Once the cell culture reached an appropriate density, cells were subcultured into a new culture vessel and/or diluted. For the application of cells in experiments the number of cells was determined with a hemocytometer. A day before transfection cells were seeded onto 6 well plates. Seeded plates were incubated at 37° C. and 5% $C0_2$, until the cells reached the appropriate confluence for the transfection. Transfection was preformed according to the manufacturer's protocol.

The HEK293T cells were transfected with commercially available plasmid pFLAG-CMV containing DNA insert coding for the wildtype SEA or for the selected split superantigen fragments in fusion with the polypeptides. The scheme of the prepared fusion proteins is shown in FIG. 1. Plasmid pFLAG-CMV contains a signal sequence for the secretion of proteins from cells that allowed the secretion of fusion proteins into the medium. Three to four days after the transfection, the medium was collected and the presence of fusion proteins in the HEK293T cell supernatant was confirmed with Western blotting.

b) Testing the Efficacy of Split Superantigen

With this embodiment, it has been shown that split superantigen has been prepared which becomes biologically active only when fused with coiled-coil forming polypeptides (FIG. 2).

To prove the biologic activity of selected split superantigen design, PBMC were stimulated with HEK293T cell supernatant containing prepared fusion proteins (FIG. 1). The methods and techniques of culturing cell cultures are well known to persons skilled in the art, therefore they are only briefly described in order to illustrate the embodiment. PBMC was obtained from the blood samples of healthy volunteers and were isolated according to the standard protocol[22]. The PBMC were cultured at 37° C. and 5% $C0_2$ and RPMI medium supplemented with 10% FBS, which contains all the necessary nutrients and growth factors, was used. The number of cells was determined with a hemocytometer. PBMC were seeded ($5*10^4$ cells/well) onto 96 well plate and after 24 hours stimulated with 100 ng/ml of commercially available SEA (Sigma-Aldrich), 50 µl of HEK293T supernatant containing recombinant wildtype SEA (rSEA) or 50 µl of split superantigen fused with polypeptides P3 or P4 (NP3, CP3, CP4), respectively, or simulated with 25 µl of each split superantigen fragments fused with polypeptides P3 or P4, combined. After 24 hour incubation at 37° C., supernatant was collected and the production of human IL-2, as an indicator of T-cell activation, was measured by commercially available ELISA assay.

Figure 1:
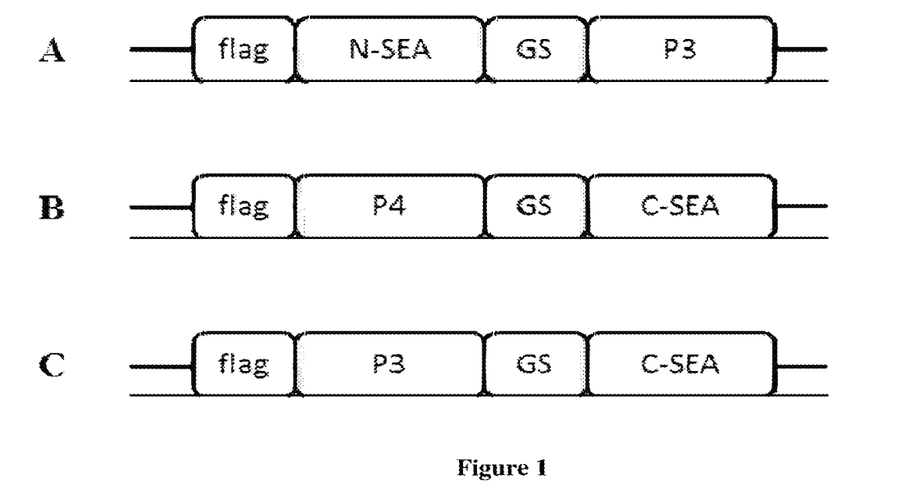
Figure 2:
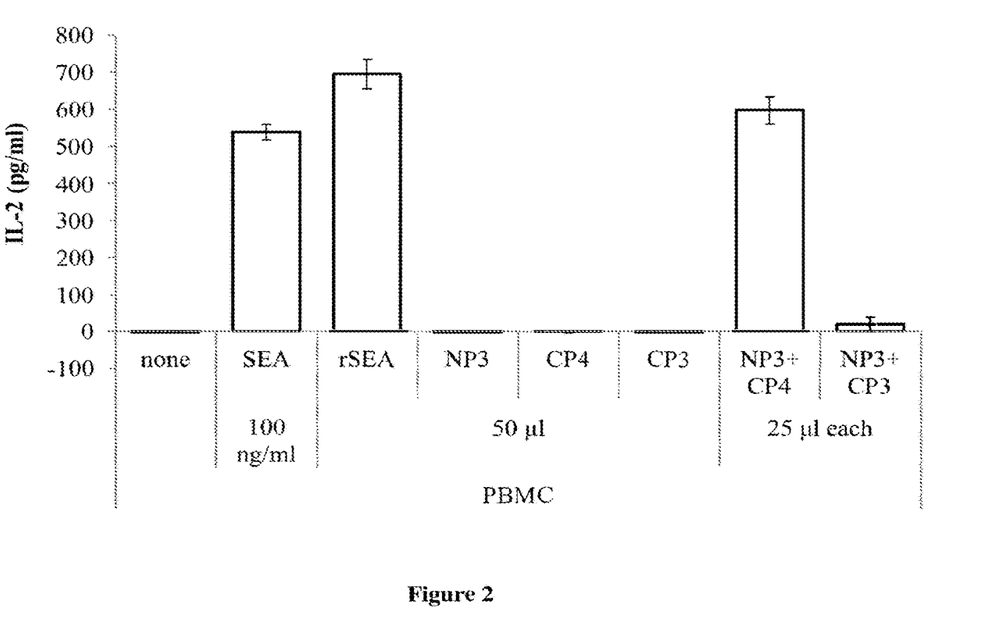
Figure 3:
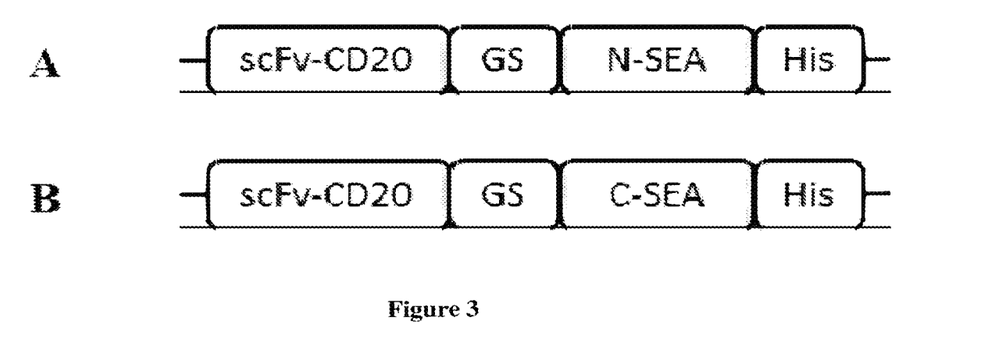
Figure 4:
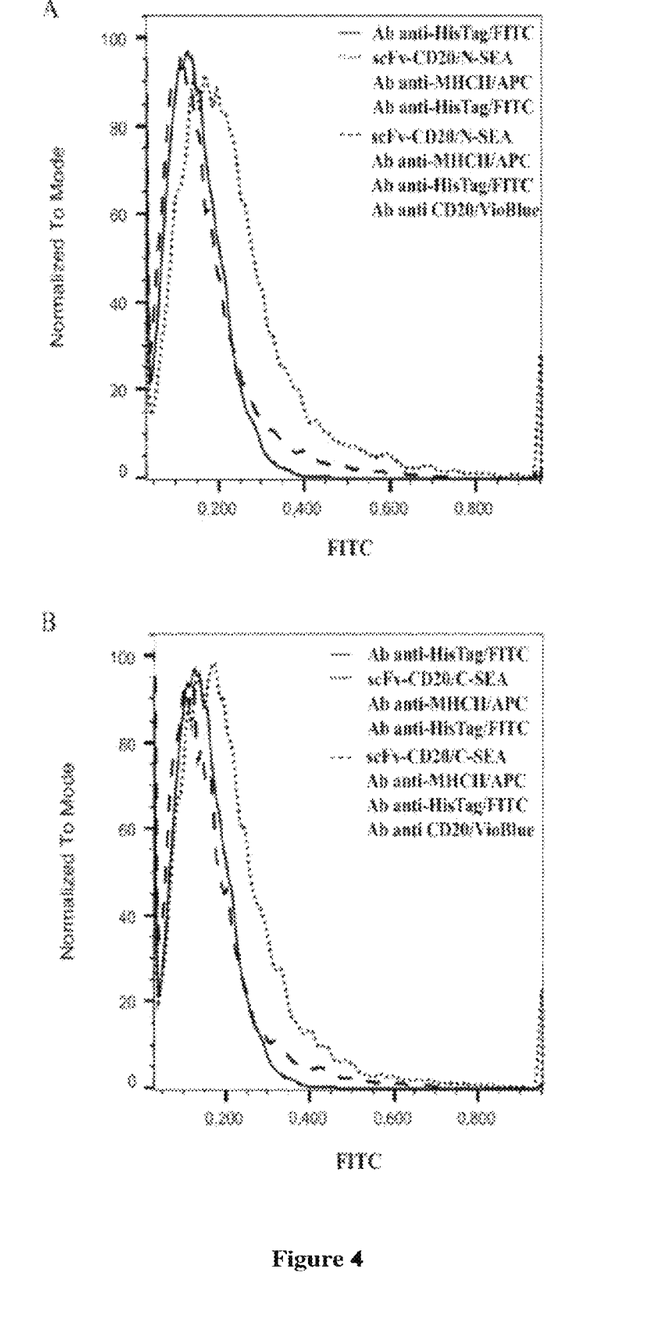
Figure 5:
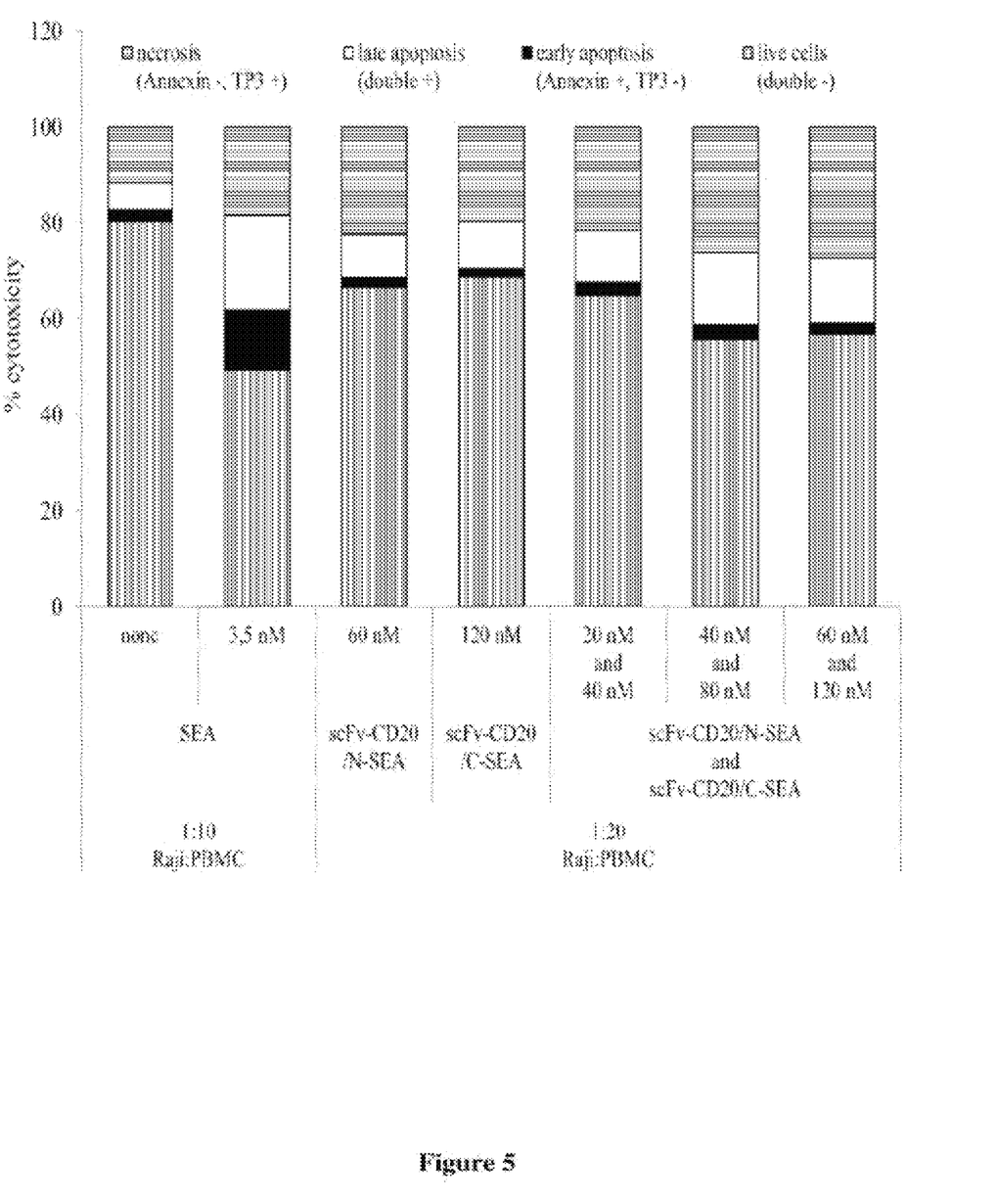

FIG. 2 show that each split superantigen fragment fused with P3 or P4 by itself does not cause T cell activation. Activation of T cells also does not occur when both split superantigen fragments are fused with P3 polypeptide, because combination of only P3 polypeptides does not dimerize and form coiled-coil. Thus when split superantigen fragments are fused as with P3 and P4 polypeptides, coiled-coil is formed, split superantigen is reconstituted and T cells are activated. With this embodiment, it has been shown that we are able to design a split superantigen, capable of activating T cell response only when fused with coiled-coil forming polypeptides, meanwhile in fusion with polypeptides that do not form coiled-coil, activation of T cells do not occur. At the same time, we have shown that the split superantigen fragments cannot spontaneously reassemble into biologically active form.

Example 3. Use of Split Superantigen for Cancer Immunotherapy c) Design of Split Superantigen Fused with Antibodies To illustrate the use of the invention for the purpose of cancer immunotherapy, the N-terminal superantigen SEA fragment (N-SEA, 1-120amino acid residues of SEA; SEQ ID: 1) and C-terminal superantigen SEA fragment (C-SEA, 112-233 amino acid residues of SEA; SEQ ID NO: 2), which overlap in nine amino acid residues, were linked with single chain variable fragment specific for tumor antigen CD20 (scFv-CD20) (SEQ ID: 6), through glycine-serine peptide linker (SEQ ID: 3).

Fusion proteins between split superantigen and scFv were prepared in the prokaryotic expression system using recombinant DNA technology. Methods and techniques for the production, isolation and refolding of recombinant proteins are well known to experts in the field and are here explained only indicative, in terms of clarifying the implementation of the embodiment.

*E. coli* strain BL21 (DE3) was transformed with a commercially available plasmid pET19b, whit inserts coding for split superantigen fragment N-SEA or C-SEA in fusion with scFv-CD20.

Scheme of the fusion proteins scFv-CD20/N-SEA and scFv-CD20/C-SEA is shown in FIG. 3. Transformed bacterial cells were grown on a solid LB medium containing ampicillin (50 μg/ml). After 16 hours incubation at 37° C., the individual bacterial colonies were put into 100 ml of a liquid medium LB containing ampicillin (50 μg/ml). Cells were incubated overnight with shaking (180 rpm) at 37° C.

Density of the bacterial cells was then determined by measuring the absorbance at a wavelength of 600 nm. Bacterial cells were cultured at 37° C. with shaking (180 rpm) in 500 ml of the liquid medium LB containing ampicillin (50 μg/ml) at the final density of the cells that corresponded to an absorbance value of $A_{600}$=0,1, until the value of $A_{600}$=0,8–1 was reached. Then the 0.2 mM IPTG was added to induce the production of recombinant fusion proteins. After 4 hours of incubation under unchanged conditions, the bacterial culture was centrifuged (10 minutes, 5000 rpm, 4° C.) and supernatant was discarded. Cell pellet was resuspended in lysis buffer (20 mM Tris-HCl, 200 mM NaCl, 1 mg/ml lysozyme, 1 mM $MgCl_2$, 1:10 000 V/V benzonase (DNase), 1:500 V/V a mixture of protease inhibitors, 10 mM imidazole, 10% glycerol) and then incubated for 1 hour at room temperature with occasional shaking. Cell lysate was centrifuged (15 minutes, 15 000 rpm, 4° C.), supernatant was discarded and pellet with inclusion bodies was stored.

Recombinant fusion proteins containing a histidine marker sequence that were produced in bacteria in the form of inclusion bodies were isolated on chelating chromatography (NiNTA agarose column) under the denaturing conditions. The inclusion bodies were washed twice with buffer (10 mM Tris-HCl, 0'1% DOC, pH 8). After each wash, the inclusion bodies were centrifuged for 15 minutes at 15 000 rpm at 4° C. Bacterial inclusion bodies were solubilized in the binding buffer (6 M GvdHCl, 100 mM NaH2PO4, 10 mM Tris-HCl, pH 8) and purified by NiNTA column that was equilibrated with the same buffer. After solubilized inclusion bodies were applied on the column, the column was incubated overnight at 4° C. with shaking, followed by washing of the column with the binding buffer alone, subsequently followed by washing with binding buffer containing 10 mM, 20 mM ter 50 mM imidazole until the absorbance measured at the wavelength of 280 nm in the caught fraction was lower than 0,02. Fusion proteins were eluted with elution buffer ((6 M GvdHCl, 100 mM NaH2PO4, 10 mM Tris-HCl, 300 mM imidazole, pH 8).

The eluted protein was dissolved in the binding buffer to a final concentration of 20-30 μg/ml ad refolding with dialysis was performed. The diluted protein was dialyzed at 4° C. three times against 2 L of 20 mM Tris-HCl, 150 mM NaCl, pH 7'5. After dialysis, the refolded protein was concentrated using commercially available concentrated falcons, and the purity of the isolated protein was confirmed by polyacrylamide electrophoresis (Coomassie staining) and Western blotting.

b) Binding of Antibody-Superantigen Fusion Proteins on Tumor Antigens on Cells

To confirm the binding of fusion proteins scFv-CD20/N-SEA and scFv-CD20/C-SEA on target CD20 antigen expressed on B cells, Raji human lymphoma cell line was used as a target cells. The methods and techniques of culturing cell cultures are well known to persons skilled in the art. Raji cells were cultured at 37° C. and 5% $CO_2$ in RMPI supplemented with 10% FBS that contains all the necessary nutrients and growth factors. Once the cell culture reached an appropriate density, cells were diluted and/or used in experiment setup. The number of cells was determined with a hemocytometer. $10^7$ Raji cells were resuspended in 80 μl PBS and, according to the manufacturer's protocol, a blocking reagent FcR and antibodies anti-HLA-DR, DP, DQ labeled with APC and/or antibodies anti-CD20 labeled with VioBlue were added. After 10 minutes incubation at 2-8° C. in dark, the cells were washed with PBS and fusion proteins scFv-CD20/N-SEA or scFv-CD20/C-SEA were added at a concentration of 150 nM. Mixture of cells and fusion proteins was incubated for 1 hour at 37° C., then washed with PBS, and incubated for 10 minutes at 2-8° C. in dark with antibodies anti-His tag labeled with FITC. Binding of fusion proteins scFv-CD20/N-SEA or scFv-CD20/C-SEA containing His tag on tumor antigen CD20 was analyzed by flow cytometry according to techniques and methods generally known to person skilled in the art.

As seen on FIG. 4, both fusion proteins scFv-CD20/N-SEA and scFv-CD20/C-SEAat a concentration of 150 nM are bound to target CD20 antigen. In all cases, Raji cells were incubated with an antibody anti-HLA-DR, DP, DQ, thereby confirming that the fusion proteins were bound to target cells via scFv-CD20 and not via superantigen fragments to the MHC class II complex. In addition, it has been shown that in the case of occupancy of targeted sites with commercially available antibody anti-CD20, the binding of fusion proteins to the CD20 antigen significantly decreases.

d) Cytotoxicity Assay

When fusion proteins bind to tumor antigens trough antibodies, the split superantigen fragments should come close enough together to reassemble into a biologically active form, recognized by TCR expressed on T cells and consequently cause tumor cell death. In this embodiment, cytotoxicity of the split superantigen fused with antibodies against tumor antigen, was determined by flow cytometry.

Human lymphoma Raji cell line was used as a target tumor cell line. Raji cells were stained with carboxyfluorescein succinimidyl ester (CFSE), according to the manufacturer's protocol, to differ between target and effector cells. Then cells were counted with a hemocytometer and seeded onto 24 well plate ($5*10^4$ cells/well). After 1 hour incubation with commercially available SEA (Sigma-Aldrich) and different concentration of fusion proteins scFv-CD20/N-SEA and scFv-CD20/C-SEA (FIG. 5), effector cells PBMC were added in ratios 1:10 and 1:20. Subsequently 48 hours later at 37° C., cells were stained with Annexin V-Pacific Blue (stains the apoptotic cells) and TO-PRO-3 (stains necrotic cells). Analysis of the viability of Raji tumor cells was performed with flow cytometer by techniques and methods generally known to those skilled in the art.

FIG. 5 shows that each fusion protein scFv-CD20/N-SEA or scFv-CD20/C-SEA alone is not cytotoxic for Raji tumor cells. Combination of both fusion proteins scFv-CD20/N-SEA and scFv-CD20/C-SEA is required to assemble the split superantigen into a biologically active form, which causes death of Raji tumor cells.

REFERENCE TO AN ELECTRONIC SEQUENCE LISTING

The contents of the electronic sequence listing (sequencelisting.txt; Size: 6 KB; and Date of Creation: Jan. 6, 2020) is herein incorporated by reference in its entirety.

LITERATURE

[1] L. M. Weiner, J. C. Murray, and C. W. Shuptrine, "Antibody-Based Immunotherapy of Cancer," *Cell*, vol. 148, no. 6, pp. 1081-184 Mar. 2012.

[2] J. S. Kang and M. H. Lee, "Overview of therapeutic drug monitoring.," *Korean J. Intern. Med.*, vol. 24, no. 1, pp. 1-10, March 2009.

[3] T. Proft and J. D. Fraser, "Bacterial superantigens," *Clin. Exp. Immunol.*, vol. 133, no. 3, pp. 299-306, 2003.

[4] J. Fraser, V. Arcus, P. Kong, E. Baker, and T. Proft, "Superantigens—powerful modifiers of the immune system," vol. 6, no. MARCH, pp. 125-132, 2000.

[5] M. D. Baker and K. R. Acharya, "Superantigens: structure-function relationships.," *Int. J. Med. Microbiol.*, vol. 293, no. 7-8, pp. 529-37, April 2004.

[6] M. Dohlsten, G. Hedlund, and T. Kalland, "Staphylococcal-enterotoxin-dependent cell-mediated cytotoxicity," *Immunol. Today*, vol. 12, pp. 147-149, 1991.

[7] M. DOHLSTEN, G. HEDLUND, E. AKERBLOM, P. A. LANDO, and T. KALLAND, "Monoclonal antibody-targeted superantigens: A different class of anti-tumor agents," *Proc. Nati. Acad. Sci. USA*, vol. 88, no. October, pp. 9287-9291, 1991.

[8] M. Dohlsten, L. Abrahmsén, P. Björk, P. a Lando, G. Hedlund, G. Forsberg, T. Brodin, N. R. Gascoigne, C. Förberg, and P. Lind, "Monoclonal antibody-superantigen fusion proteins: tumor-specific agents for T-cell-based tumor therapy.," *Proc. Natl. Acad. Sci. U.S.A.*, vol. 91, no. 19, pp. 8945-9, September 1994.

[9] M. Dohlsten, L. Abrahmsén, L. Ohlsson, and P. Lind, "Immunotherapy of human colon cancer by antibody-targeted superantigens," vol. 41, pp. 162-168, 1995.

[10] B. J. Giantonio, R. K. Alpaugh, J. Schultz, C. McAleer, D. W. Newton, B. Shannon, Y. Guedez, M. Kotb, L. Vitek, R. Persson, P. O. Gunnarsson, T. Kalland, M. Dohlsten, B. Persson, and L. M. Weiner, "Superantigen-based immunotherapy: a phase I trial of PNU-214565, a monoclonal antibody-staphylococcal enterotoxin A recombinant fusion protein, in advanced pancreatic and colorectal cancer.," *J. Clin. Oncol.*, vol. 15, no. 5, pp. 1994-2007 May 1997.

[11] H. Borghaci, K. Alpaugh, G. Hedlund, G. Forsberg, C. Langer, A. Rogatko, R. Hawkins, S. Dueland, U. Lassen, and R. B. Cohen, "Phase I dose escalation, pharmacokinetic and pharmacodynamic study of naptumomab estafenatox alone in patients with advanced cancer and with docetaxel in patients with advanced non-small-cell lung cancer.," *J. Clin. Oncol.*, vol. 27, no. 25, pp. 4116-23, September 2009.

[12] M. Dohlsten, T. Kalland, P. Gunnarsson, P. Antonsson, a Molander, J. Olsson, R. d'Argy, L. Ohlsson, M. Soegaard, R. Persson, and T. Brodin, "Man-made superantigens: Tumor-selective agents for T-cell-based therapy.," *Adv. Drug Deliv. Rev.*, vol. 31, no. 1-2, pp. 131-142, April 1998.

[13] E. Erlandsson, K. Andersson, A. Cavallin, A. Nilsson, U. Larsson-Lorek, U. Niss, A. Sjöberg, M. Wallen-Öhman, P. Antonsson, B. Walse, and G. Forsberg, "Identification of the antigenic epitopes in staphylococcal enterotoxins A and E and design of a superantigen for human cancer therapy," *J. Mol. Biol.*, vol. 333, no. 5, pp. 893-905, 2003.

[14] C. Gidlof, M. Dohlsten, P. Lando, T. Kalland, C. Sundstrom, and T. H. Totterman, "A Superantigen-Antibody Fusion Protein for T-Cell Immunotherapy of Human B-Lineage Malignancies," *Blood*, vol. 89, pp. 2089-2097, 1997.

[15] G. Forsberg, L. Ohlsson, T. Brodin, P. Björk, P. A. Lando, D. Shaw, P. L. Stern, and M. Dohlsten, "Therapy of human non-small-cell lung carcinoma using antibody targeting of a modified superantigen," vol. 85, pp. 129-136, 2001.

[16] L. Abrahmsen, M. Dohlsten, S. Segrén, P. Björk, E. Jonsson, and T. Kalland, "Characterization of two distinct MHC class II binding sites in the superantigen staphylococcal enterotoxin A," *Embo J.*, vol. 14, no. 13, pp. 2978-2986, 1995.

[17] Q. Tong, K. Liu, X.-M. Lu, X.-G. Shu, and G.-B. Wang, "Construction and characterization of a novel fusion protein MG7-scFv/SEB against gastric cancer.," *J. Biomed. Biotechnol.*, vol. 2010, p. 121094, January 2010.

[18] S. S. Shekhawat and I. Ghosh, "Split-protein systems: beyond binary protein-protein interactions.," *Curr. Opin. Chem. Biol.*, vol. 15, no. 6, pp. 789-97, December 2011.

[19] K. P. Kent, W. Childs, S. G. Boxer, and S. U. V, "Deconstructing Green Fluorescent Protein that it can be directly observed by electrospray time-of-flight mass," pp. 9664-9665, 2008.

[20] L. Dong, L.-B. Lv, and R. Lai, *Molecular cloning: A laboratory manual,* 4th ed., vol. 1, no. 1. 2012.

[21] H. Gradišar and R. Jerala, "De novo design of orthogonal peptide pairs forming parallel coiled-coil heterodimers.," *J. Pept. Sci.*, vol. 17, no. 2, pp. 100-6, February 2011.

[22] Biotec Miltenyi, "Isolation of mononuclear cells from human peripheral blood by density gradient centrifugation," *Miltenyibiotec.Com,* 2008. [Online]. Available: https://www.miltenyibiotec.com/~/media/Files/Navigation/Research/Stem Cell/SP_MC_PB_density_gradient.ashx.

---

The invention claimed is:

1. A set of two fusion proteins, each comprising a non-functional fragment of a superantigen fused with proteins,
   wherein the proteins comprise antigen-binding moieties, the antigen-binding moieties being antibodies or antigen-binding fragments thereof, to trigger dimerization of the non-functional fragments into a biologically active form with superantigen function upon contact with a target cell,
   wherein the superantigen is staphylococcal enterotoxin A (SEA) from *Staphylococcus aureus*,
   wherein the first non-functional fragment is an N-terminal fragment of said superantigen and comprises the entire amino acid as shown in SEQ ID NO: 1 and the second non-functional fragment is a C-terminal fragment of said superantigen and comprises the entire amino acid as shown in SEQ ID NO: 2, and
   wherein each of the two fusion proteins further comprises a flexible glycine serine peptide linker, the linker comprised of 10 to 15 amino acids, which fuses the non-functional fragment of the superantigen with the proteins.

2. The set of two fusion proteins according to claim 1, wherein the non-functional fragments are fused with the proteins through gene fusion or chemical conjugation, wherein the gene fusion or chemical conjugation is to the N-terminus or C-terminus of the non-functional fragments.

3. The set of two fusion proteins according to claim 1, wherein the set of two fusion proteins are expressed and secreted from human cells.

4. A DNA molecule coding for the set of two fusion proteins according to claim 1.

5. A pharmaceutical composition comprising the set of two fusion proteins according to claim 1.

6. The set of two fusion proteins according to claim 1, wherein the proteins that trigger the dimerization are antibodies or antibody fragments specific for cell surface proteins on the target cell.

7. A pharmaceutical composition for cancer immunotherapy, comprising the set of two fusion proteins according to claim 1, wherein the target cell is a cancer cell.

* * * * *

SEQUENCE LISTING

```
<160> NUMBER OF SEQ ID NOS: 6

<210> SEQ ID NO 1
<211> LENGTH: 120
<212> TYPE: PRT
<213> ORGANISM: Staphylococcus aureus

<400> SEQUENCE: 1

Ser Glu Lys Ser Glu Glu Ile Asn Glu Lys Asp Leu Arg Lys Lys Ser
1               5                   10                  15

Glu Leu Gln Gly Thr Ala Leu Gly Asn Leu Lys Gln Ile Tyr Tyr Tyr
                20                  25                  30

Asn Glu Lys Ala Lys Thr Glu Asn Lys Glu Ser His Asp Gln Phe Leu
            35                  40                  45

Gln His Thr Ile Leu Phe Lys Gly Phe Phe Thr Asp His Ser Trp Tyr
        50                  55                  60

Asn Asp Leu Leu Val Asp Phe Asp Ser Lys Asp Ile Val Asp Lys Tyr
65                  70                  75                  80

Lys Gly Lys Lys Val Asp Leu Tyr Gly Ala Tyr Tyr Gly Tyr Gln Cys
                85                  90                  95

Ala Gly Gly Thr Pro Asn Lys Thr Ala Cys Met Tyr Gly Gly Val Thr
            100                 105                 110

Leu His Asp Asn Asn Arg Leu Thr
            115                 120

<210> SEQ ID NO 2
<211> LENGTH: 122
<212> TYPE: PRT
<213> ORGANISM: Staphylococcus aureus

<400> SEQUENCE: 2

Thr Leu His Asp Asn Asn Arg Leu Thr Glu Glu Lys Lys Val Pro Ile
1               5                   10                  15

Asn Leu Trp Leu Asp Gly Lys Gln Asn Thr Val Pro Leu Glu Thr Val
                20                  25                  30

Lys Thr Asn Lys Lys Asn Val Thr Val Gln Glu Leu Asp Leu Gln Ala
            35                  40                  45

Arg Arg Tyr Leu Gln Glu Lys Tyr Asn Leu Tyr Asn Ser Asp Val Phe
        50                  55                  60

Asp Gly Lys Val Gln Arg Gly Leu Ile Val Phe His Thr Ser Thr Glu
65                  70                  75                  80

Pro Ser Val Asn Tyr Asp Leu Phe Gly Ala Gln Gly Gln Tyr Ser Asn
                85                  90                  95

Thr Leu Leu Arg Ile Tyr Arg Asn Lys Thr Ile Asn Ser Glu Asn
            100                 105                 110

Met His Ile Asp Ile Tyr Leu Tyr Thr Ser
            115                 120

<210> SEQ ID NO 3
<211> LENGTH: 33
<212> TYPE: PRT
<213> ORGANISM: Unknown
```

```
<220> FEATURE:
<223> OTHER INFORMATION: Peptide

<400> SEQUENCE: 3

Ser Pro Glu Asp Glu Ile Gln Gln Leu Glu Glu Ile Ala Gln Leu
1               5                   10                  15

Glu Gln Lys Asn Ala Ala Leu Lys Glu Lys Asn Gln Ala Leu Lys Tyr
                20                  25                  30

Gly

<210> SEQ ID NO 4
<211> LENGTH: 33
<212> TYPE: PRT
<213> ORGANISM: Unknown
<220> FEATURE:
<223> OTHER INFORMATION: Peptide

<400> SEQUENCE: 4

Ser Pro Glu Asp Lys Ile Ala Gln Leu Lys Gln Lys Ile Gln Ala Leu
1               5                   10                  15

Lys Gln Glu Asn Gln Gln Leu Glu Glu Glu Asn Ala Ala Leu Glu Tyr
                20                  25                  30

Gly

<210> SEQ ID NO 5
<211> LENGTH: 245
<212> TYPE: PRT
<213> ORGANISM: Homo sapiens

<400> SEQUENCE: 5

Gln Val Gln Leu Gln Gln Ser Gly Ala Glu Val Lys Lys Pro Gly Ser
1               5                   10                  15

Ser Val Lys Val Ser Cys Lys Ala Ser Gly Tyr Thr Phe Thr Ser Tyr
                20                  25                  30

Asn Met His Trp Val Lys Gln Ala Pro Gly Gln Gly Leu Glu Trp Ile
                35                  40                  45

Gly Ala Ile Tyr Pro Gly Asn Gly Asp Thr Ser Tyr Asn Gln Lys Phe
50                      55                  60

Lys Gly Lys Ala Thr Leu Thr Ala Asp Glu Ser Thr Asn Thr Ala Tyr
65                  70                  75                  80

Met Glu Leu Ser Ser Leu Arg Ser Glu Asp Thr Ala Phe Tyr Tyr Cys
                85                  90                  95

Ala Arg Ser Thr Tyr Tyr Gly Gly Asp Trp Tyr Phe Asp Val Trp Gly
                100                 105                 110

Gln Gly Thr Thr Val Thr Val Ser Ser Gly Ser Thr Ser Gly Ser Gly
                115                 120                 125

Lys Pro Gly Ser Gly Glu Gly Ser Thr Lys Gly Asp Ile Gln Leu Thr
                130                 135                 140

Gln Ser Pro Ser Ser Leu Ser Ala Ser Val Gly Asp Arg Val Thr Met
145                 150                 155                 160

Thr Cys Arg Ala Ser Ser Ser Val Ser Tyr Ile His Trp Phe Gln Gln
                165                 170                 175

Lys Pro Gly Lys Ala Pro Lys Pro Trp Ile Tyr Ala Thr Ser Asn Leu
                180                 185                 190

Ala Ser Gly Val Pro Val Arg Phe Ser Gly Ser Gly Ser Gly Thr Asp
                195                 200                 205

Tyr Thr Phe Thr Ile Ser Ser Leu Gln Pro Glu Asp Ile Ala Thr Tyr
```

-continued

```
            210                 215                 220
Tyr Cys Gln Gln Trp Thr Ser Asn Pro Pro Thr Phe Gly Gly Gly Thr
225                 230                 235                 240

Lys Leu Glu Ile Lys
                245

<210> SEQ ID NO 6
<211> LENGTH: 10
<212> TYPE: PRT
<213> ORGANISM: Unknown
<220> FEATURE:
<223> OTHER INFORMATION: Peptide

<400> SEQUENCE: 6

Gly Gly Gly Gly Ser Gly Gly Gly Gly Ser
1               5                   10
```